(12) United States Patent
Yamada et al.

(10) Patent No.: US 6,936,241 B2
(45) Date of Patent: Aug. 30, 2005

(54) SUNSCREEN COMPOSITION

(75) Inventors: Kosaku Yamada, Shiga (JP); Chieko Soh, Ashiya Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 361 days.

(21) Appl. No.: 10/216,118

(22) Filed: Aug. 9, 2002

(65) Prior Publication Data

US 2003/0064037 A1 Apr. 3, 2003

Related U.S. Application Data

(60) Provisional application No. 60/353,282, filed on Feb. 1, 2002.

(30) Foreign Application Priority Data

Aug. 17, 2001 (WO) .............................. PCT/US01/25707

(51) Int. Cl.$^7$ ............................ A61K 7/42; A61K 7/44; A61K 7/021; A61K 7/035
(52) U.S. Cl. ............................ 424/59; 424/60; 424/63; 424/69; 424/400; 424/401
(58) Field of Search ............................ 424/59, 60, 400, 424/401, 63, 69

(56) References Cited

U.S. PATENT DOCUMENTS

| | | |
|---|---|---|
| 4,937,370 A | 6/1990 | Sabatelli |
| 4,999,186 A | 3/1991 | Sabatelli et al. |
| 5,073,371 A | 12/1991 | Turner et al. |
| 5,073,372 A | 12/1991 | Turner et al. |
| 5,087,445 A | 2/1992 | Haffey et al. |
| 5,188,831 A * | 2/1993 | Nicoll et al. ................. 424/401 |
| 5,362,482 A | 11/1994 | Yoneyama et al. |
| 5,429,816 A | 7/1995 | Hofrichter et al. |

FOREIGN PATENT DOCUMENTS

| | | |
|---|---|---|
| EP | 0661334 A1 | 12/1984 |
| JP | 2691729 B2 | 6/1988 |
| JP | 2665473 B2 | 9/1988 |
| JP | H7-61907 A | 3/1995 |
| JP | H-2996410 B | 3/1995 |
| JP | H7-165533 A | 6/1995 |
| JP | H9-263524 A | 10/1997 |
| WO | WO 99/04753 A1 | 2/1999 |
| WO | WO 01/91704 A1 | 12/2001 |

* cited by examiner

Primary Examiner—Shelley A. Dodson
(74) Attorney, Agent, or Firm—Juliet A. Jones; Eileen L. Hughett; John M. Howell

(57) ABSTRACT

Disclosed is a water-in-oil emulsified sunscreen composition comprising by weight:

(a) an effective amount of a UV protection agent;
(b) from about 0.1% to about 70% of a non-thickening oil absorbing powder having a mineral oil absorbing ability of at least about 40 ml/100 g;
(c) at least about 10% of the entire composition of water; and
(d) an oil phase comprising:
  (i) at least about 50% by weight of the oil phase of a volatile silicone oil; and
  (ii) from about 0.1% to less than the oil absorbing ability of the non-thickening oil absorbing powder of a non-volatile oil; wherein when the UV protection agent is a non-volatile liquid of hydrophobic nature, it is considered the non-volatile oil.

9 Claims, No Drawings

SUNSCREEN COMPOSITION

CROSS REFERENCE TO RELATED APPLICATION

This application claims the benefit of U.S. Provisional Application No. 60/353,282, filed Feb. 1, 2002.

FIELD OF THE INVENTION

The present invention relates to water-in-oil emulsified sunscreen compositions which provide effective UV protection benefit, while also providing a fresh, cool, non-greasy feeling to the skin. In particular, the present invention relates to water-in-oil emulsified sunscreen compositions which can be used as a make-up base.

BACKGROUND

Excessive exposure of the skin to sunlight is known to cause skin damage and skin disorders such as scaling and texture changes of the stratum corneum. Excessive and/or chronic exposure of the skin to sunlight is also known to accelerate skin ageing. In order to prevent such skin disorders, sunscreen compositions containing ultraviolet light (UV) protecting agents at controlled safe and effective levels are available for skin use. UV protection agents having different chemical/physical properties are available, for example, organic and inorganic, hydrophobic and hydrophilic. Many sunscreen compositions available on the market are oil-based so that the composition is not easily worn away by perspiration and/or water.

In that sunscreen compositions are more frequently used during warm seasons, such as in the summer, consumers desire a fresh, cool feeling to the skin upon use of sunscreen compositions. Such desire is particularly strong for consumers who use sunscreen compositions on a daily basis. However, in that sunscreen compositions are usually oil-based, it is generally difficult to provide such fresh, cool feeling to the skin. Rather, sunscreen compositions tend to impart a greasy feel to the skin. The perception of such negative skin feels may be particularly true for consumers having oily skin, and/or consumers who live in tropic or semi-tropic areas. Sunscreen compositions such as those disclosed in Japanese Patent Publications A-7-165533 and A-9-263524 have been proposed. While such sunscreen compositions may provide sunscreen benefits, further improvement is desired in view of skin feel.

Yet another desire of the consumer is to have a sunscreen composition that is easy to apply and not messy upon use. In view of the composition being oil-based and/or containing a certain amount of metallic oxides, applying sunscreen composition to the skin may leave the hands and fingers greasy and/or with white residues. This may lead the consumer to wash his/her hands, thereby adding another step for applying a sunscreen composition. Such additional step is unfavorable in a daily skin care regimen.

Meanwhile, the use of sunscreen compositions, particularly in the form of lotions and creams, as foundation bases are known. "Foundation base" products are products to be applied on the skin prior to applying the foundation, and are increasing popularity in Asian countries such as Japan. Foundation bases are used for enhancing the performance of the foundation, and thus are typically designed for increasing spreadability of the foundation and increasing attachment of the foundation. Foundation bases should not affect the performance of the foundation to be applied on top of it. In this respect, it is generally desirable that the foundation base has controlled affinity and solubility with the foundation. Foundation bases which further provide UV protection benefits are convenient for the consumer.

Based on the foregoing, there is a need for a sunscreen composition which provides effective UV protection benefit, while leaving a fresh, cool, non-greasy feeling to the skin, even for consumers having oily skin. There is also a need for a sunscreen composition which is easy to apply and not messy upon use. There is also a need for a sunscreen composition which can be suitably used as a foundation base product.

None of the existing art provides all of the advantages and benefits of the present invention.

SUMMARY

The present invention is directed to a water-in-oil emulsified sunscreen composition comprising by weight:
(a) an effective amount of a UV protection agent;
(b) from about 0.1% to about 70% of a non-thickening oil absorbing powder having a mineral oil absorbing ability of at least about 40 ml/100 g;
(c) at least about 10% of the entire composition of water; and
(d) an oil phase comprising:
  (i) at least about 50% by weight of the oil phase of a volatile silicone oil; and
  (ii) from about 0.1% to less than the oil absorbing ability of the non-thickening oil absorbing powder of a non-volatile oil; wherein when the UV protection agent is a non-volatile liquid of hydrophobic nature, it is considered the non-volatile oil;
which satisfies the need for a sunscreen composition which provides effective UV protection benefit, while leaving a fresh, cool, non-greasy feeling to the skin, even for consumers having oily skin.

These and other features, aspects, and advantages of the present invention will become evident to those skilled in the art from a reading of the present disclosure with the appended claims.

DETAILED DESCRIPTION

The following is a list of definitions for terms used herein.

"Comprising" means that other steps and other ingredients which do not affect the end result can be added. This term encompasses the terms "consisting of" and "consisting essentially of".

All percentages are by weight of total composition unless specifically stated otherwise.

All cited references are incorporated herein by reference in their entireties.

Citation of any reference is not an admission regarding any determination as to its availability as prior art to the claimed invention.

All ratios are weight ratios unless specifically stated otherwise.

The present invention, in its product and process aspects, is described in detail as follows.

UV Protecting Agent

The composition of the present invention comprises a safe and effective amount, of a UV protecting agent, preferably at a level of from about 0.5% to about 40%, more preferably from about 1% to about 20% by weight of the entire composition. Two or more UV protecting agents may be, and are preferably used to provide a wide spectrum of protection in the UV region. For example, a combination of at least 1 UV protecting agent which mainly provides protection from UVA lights, and at least 1 UV protecting agent which mainly provide protection from UVB lights, may be used.

A wide variety of conventional UV protecting agent are suitable for use herein. See, U.S. Pat. No. 5,087,445, Haffey et al, issued Feb. 11, 1992; U.S. Pat. No. 5,073,372, Turner et al, issued Dec. 17, 1991; U.S. Pat. No. 5,073,371, Turner et al., issued Dec. 17, 1991; and Segarin, et al, at Chapter VIII, pages 189 et seq., of Cosmetics Science and Technology (1972), which discloses numerous suitable UV protecting agent. Preferred among those UV protecting agent which are useful in the emulsions are those selected from 2-ethylhexyl-p-methoxycinnamate (commercially available as PARSOL MCX), butylmethoxyd ibenzoyl-methane, 2-hydroxy-4-methoxybenzo-phenone, 2-phenylbenzimidazole-5-sulfonic acid, octyldimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide such as MT-100 available from Tayca, zinc oxide, silica, iron oxide, Eusolex™ 6300, Octocrylene, Parsol 1789, and mixtures thereof.

Among these UV protecting agents, inorganic UV protecting agents such as titanium dioxide and zinc oxide can be coated by one or more coating materials for providing a variety of properties to the inorganic UV protecting agents, for example, for providing hydrophobicity to the surface of the inorganic UV protecting agents, for providing a greater net charge than the zeta potential of the inorganic UV protecting agents, and for providing both hydrophobicity and a greater net charge.

The coating materials which provide hydrophobicity to the surface of the inorganic UV protecting agents include, for example, silicone, fluorine, metallic soap, and fatty acid. Hydrophobically coated inorganic UV protecting agents are preferably used in the present invention in view of providing effective UV protecting benefit. Commercially available hydrophobically coated inorganic UV protecting agents useful herein include, for example, methicone and aluminium hydroxide treated micro titanium dioxide with a tradename SI-TTO-S-3-Z LHC available from Miyoshi Kasei, dimethicone and myristic acid treated micro zinc oxide with a tradename SAMT-UFZO-450 available from Miyoshi Kasei, and dimethicone treated micro zinc oxide with a tradename Z-Cote HP-1 available from BASF.

With respect to providing greater net charge, any coating material can be used as long as the net charge (cationic or anionic) conferred to the inorganic UV protecting agents is greater than the untreated inorganic UV protecting agents. Nonlimiting examples of coating materials that confer a cationic charge include cationic polymers (natural and/or synthetic) and cationic surfactants. Preferred cationic coating materials are selected from the group consisting of chitosan, hydroxypropyl chitosan, quaternium-80, polyquaternium-7, and mixtures thereof. Nonlimiting examples of coating materials that confer an anionic charge include anionic polymers (natural and/or synthetic) and anionic surfactants. Preferred anionic coating materials are selected from the group consisting of ammonium polyacrylate, sodium polyacrylate, and mixtures thereof.

Particularly useful herein are UV protecting agents such as those disclosed in U.S. Pat. No. 4,937,370, Sabatelli, issued Jun. 26, 1990, and U.S. Pat. No. 4,999,186, Sabatelli, issued Mar. 12, 1991. The UV protecting agent disclosed therein have, in a single molecular, two distinct chromophore moieties which exhibit different ultraviolet radiation absorption spectra. One of the chromophore moieties absorbs predominantly in the UVB radiation range and the other absorbs strongly in the UVA radiation range. These UV protecting agent provide higher efficacy, broader UV absorption, lower skin penetration and longer lasting efficacy relative to conventional UV protecting agent.

Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978.

Non-Thickening Oil Absorbing Powder

The compositions of the present invention comprise a non-thickening oil absorbing powder at a level of from about 0.1% to about 70%, preferably from of from about 1% to about 50%, more preferably from about 5% to about 30%, by weight of the entire composition. The non-thickening oil absorbing powders of the present invention are those which have a mineral oil absorbing ability of at least about 40 ml/100 g. When a combination of non-thickening oil absorbing powders are used, each powder has a mineral oil absorbing ability of at least about 40 ml/100 g.

Mineral oil absorbing ability is measured based on JIS K5101, with replacement of linseed oil to mineral oil. A suitable mineral oil material useful for this measurement is Carnation White Mineral Oil available from by Witco chemical. First, about 1–5 g of sample powder is placed on a glass plate. The weight of sample powder is expressed as "sample(g)". Mineral oil is dropped in small amounts to the sample powder, after which the treated sample powder is mixed and kneaded using a spatula. The same operation is repeated until the treated sample powder forms a retainable shape. The voluminous amount of mineral oil used to reach such retainable shape is measured, and expressed as "paraffin(ml)". The following formula is used to calculate the mineral oil absorbing ability of a powder: {paraffin(ml)× 100}/sample (g).

The non-thickening oil absorbing powders of the present invention are absent of thickening properties when in contact with any volatile or nonvolatile oil, such as seen in certain cosmetic powders. Cosmetic powders having thickening properties, and thus not preferable for use as non-thickening oil absorbing powders herein are, for example, silica dimethyl silylate, bentonite, hectorite, magnesium aluminum silicate, and fumed silica. The non-thickening property is important for the non-thickening oil absorbing powders herein, as thickening may lead to deteriorating the fresh feeling, or even worse, providing a negative sticky feel to the skin. The non-thickening oil absorbing powders of the present invention are capable of absorbing the non-volatile oils included in the present compositions, such non-volatile oils containing UV protecting agents which are non-volatile fluids, and are hydrophobic. The non-volatile oils, include those which have UV protecting effect, are the components that are mainly attributed of giving the negative greasy feeling of conventional UV protection products. By absorbing such non-volatile oils, the non-volatile oils have a less chance of directly touching the skin upon application of the present composition to the skin. The UV protection efficacy of the UV protection agents that are non-volatile oils is generally not effected by being absorbed in powder. The non-thickening oil absorbing powders are contained at level such that the oil absorbing ability of the non-thickening oil absorbing powder is greater than the total amount of non-volatile oils.

It is understood to one skilled in the art that some of the metallic oxide UV protection agents may have a certain level of oil absorbing ability. However, regardless of its oil absorbing ability, UV protection agents are not considered as a non-thickening oil absorbing powder of the present invention. In the present invention, powders having oil absorbing ability, on top of the UV protection agents, are essential in order to provide controlled coverage.

Nonlimiting examples of non-thickening oil absorbing powders include silica, boron nitride, polyamide resin powders such as nylon powder, mica, sericite, kaolin, talc, iron oxide, alumina zirconia, aluminum silicate, barium silicate, calcium silicate, magnesium silicate, zeolite, barium sulfate, calcium phosphate hydroxide, polyethylene powder, methyl polymethacrylate powder, polystyrene powder, cellulose powder, bismuth oxychloride, and the same powders which are surface treated with hydrophobic material such as silicone, fluorine, metallic soap, and fatty acid.

Highly preferable non-thickening oil absorbing powders that are commercially available include silicone-treated silica by the tradename of SASB-300 available from Miyoshi Kasei, boron nitride and nylon powder SP500 available from Toray.

The solid silicone elastomer powders are also useful as non-thickening oil absorbing powders. The solid silicone elastomer powder herein is to be distinguished from silicone elastomers which provide a gel when in contact with silicone oils.

Useful herein are solid silicone elastomer powders that are fine particles of a silicone rubber of which the particles have a composite structure as disclosed in EP 661,334 A publication. These fine particles of a silicone rubber of which the particles have a composite structure consist of a spherical or globular particle of a cured silicone rubber having an average particle diameter in the range from 0.1 to 100 μm and a coating layer of a polyorganosilsesquioxane resin, the coating amount of the polyorganosilsesquioxane resin being in the range from 1 to 500 parts by weight per 100 parts by weight of the silicone rubber particles before coating.

The silicone rubber forming the fine core particles, on which the coating layer of the polyorganosilsesquioxane resin is formed, is a cured diorganopolysiloxane having linear diorganopolysiloxane segments represented by the general formula in which each R is, independently from the others, an unsubstituted or substituted monovalent hydrocarbon group having 1 to 20 carbon atoms exemplified by alkyl groups such as methyl, ethyl, propyl and butyl groups, aryl groups such as phenyl and tolyl groups, alkenyl groups such as vinyl and allyl groups and aralkyl groups such as 2-phenylethyl and 2-phenylpropyl groups as well as those substituted hydrocarbon groups obtained by replacing a part or all of the hydrogen atoms in the above named hydrocarbon groups with substituents including halogen atoms, epoxy group, amino group, mercapto group, (meth)acryloxy group and the like such as chloromethyl and 3,3,3-trifluoropropyl groups, at least 90% by moles of the groups R being preferably methyl groups, and the subscript a is a positive integer in the range, though not particularly limitative, from 5 to 5000 or, preferably, from 10 to 1000. Such value of the subscript is selected so that the silicone rubber particles after coating with the silicone resin can impart the matrix material compounded therewith with an adequate internal stress and improved surface lubricity while, difficulties are not encountered in the preparation of silicone rubber particles. It is optional that the silicone rubber forming the fine particles is compounded with a silicone oil, organosilane compound, inorganic and organic powders and the like.

Commercially available solid silicone elastomer powders highly useful herein include vinyl dimethicone/methicone silsesquioxane crosspolymer with tradenames KSP series available from ShinEtsu Chemical Co., Ltd., Tokyo Japan, and hardened polyorgano siloxane elastomers with tradenames Trefil series available from Toray Dow Corning.

Water

The composition of the present invention comprises water in an amount by weight of at least about 10%, preferably from about 10% to about 80%, more preferably from about 10% to about 40%, of the entire composition.

Without being bound by theory, the species and levels of water herein is believed to provide improved fresh and cool feeling to the skin. Further, this amount of water allows the inclusion of water-soluble skin treatment agents such as niacinamide.

In the present invention, deionized water is typically used. Water from natural sources including mineral cations can also be used, depending on the desired characteristic of the product.

Oil Phase

The composition of the present invention comprises an oil phase which, together with water, provides a water-in-oil emulsion form of the present invention. "Oil phase" means any liquid oils that are not water-soluble, and that are not powders or pigments.

The oil phase comprises at least a volatile silicone oil. Even when other oil phase components are included, the volatile silicone oil makes at least about 50% by weight of the oil phase. Other components that may be comprised in the oil phase are other volatile oils and non-volatile oils.

Volatile Silicone Oil

The oil phase comprises a volatile silicone oil by weight of the oil phase at a level of at least 50%, preferably at least about 60%, more preferably at least about 70%. Without being bound by theory, the species and levels of the volatile silicone oil herein is believed to provide improved fresh, cool, and non-greasy feeling to the skin, without necessarily leaving a dried feeling to the skin.

The volatile silicone oil useful herein are selected from those having a boiling point of from about 60 to about 260° C., preferably those having from 2 to 7 silicon atoms.

The volatile silicone oils useful herein include polyalkyl or polyaryl siloxanes with the following structure (I):

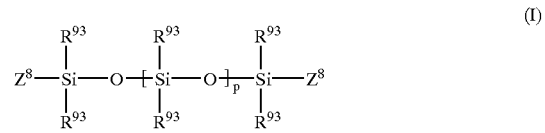

(I)

wherein $R^{93}$ is independently alkyl or aryl, and p is an integer from about 0 to about 5. $Z^8$ represents groups which block the ends of the silicone chains. Preferably, $R^{93}$ groups include methyl, ethyl, propyl, phenyl, methylphenyl and phenylmethyl, $Z^8$ groups include hydroxy, methyl, methoxy, ethoxy, propoxy, and aryloxy. More preferably, $R^{93}$ groups and $Z^8$ groups are methyl groups. The preferred volatile silicone compounds are hexamethyldisiloxane, octamethyltrisiloxane, decamethyltetrasiloxane, hexadecamethylheptasiloxane. Commercially available volatile silicone compounds useful herein include octamethyltrisiloxane with tradename SH200C-1cs, decamethyltetrasiloxane with tradename SH200C-1.5cs, hexadecamethylheptasiloxane with tradename SH200C-2cs, all available from Dow Corning.

The volatile silicone oils useful herein also include a cyclic silicone compound having the formula:

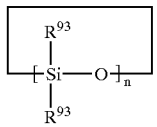

wherein $R^{93}$ is independently alkyl or aryl, and n is an integer of from 3 to 7.

Preferably, $R^{93}$ groups include methyl, ethyl, propyl, phenyl, methylphenyl and phenylmethyl. More preferably, $R^{93}$ groups are methyl groups. The preferred volatile silicone compounds are octamethylcyclotetrasiloxane, decamethylcyclopentasiloxane, tetradecamethylcyclohexasiloxane. Commercially available volatile silicone compounds useful herein include octamethylcyclotetrasiloxane with tradename SH244, decamethylcyclopentasiloxane with tradename DC245 and SH245, and dodeamethylcyclohexasiloxane with tradename DC246; all available from Dow Corning.

Non-Volatile Oil

The oil phase may comprise a non-volatile oil by weight of the oil phase at a level of from about 0.1% to less than the oil absorbing ability of the non-thickening oil absorbing powder of a non-volatile oil, preferably from about 0.1% to about 40%, more preferably from about 0.1% to about 30%. For purposes of comparing the oil absorbing ability, wherein when the UV protection agent is a non-volatile liquid of hydrophobic nature, it is considered a non-volatile oil. The non-volatile oils herein are those which provide an emollient benefit to the skin.

Non-volatile oils useful herein are, for example, isotridecyl isononanoate, isostearyl isostearate, isocetyl isosteatrate, isopropyl isostearate, isodecyl isonoanoate, cetyl octanoate, isononyl isononanoate, diisopropyl myristate, isocetyl myristate, isotridecyl myristate, isopropyl myristate, isostearyl palmitate, isocetyl palmitate, isodecyl palmitate, isopropyl palmitate, octyl palmitate, caprylic/capric acid triglyceride, glyceryl tri-2-ethylhexanoate, neopentyl glycol di(2-ethyl hexanoate), diisopropyl dimerate, tocopherol, tocopherol acetate, avocado oil, camellia oil, turtle oil, macadamia nut oil, corn oil, mink oil, olive oil, rapeseed oil, eggyolk oil, sesame oil, persic oil, wheat germ oil, pasanqua oil, castor oil, linseed oil, safflower oil, cotton seed oil, perillic oil, soybean oil, peanut oil, tea seed oil, kaya oi., rice bran oil, china paulownia oi., Japanese paulownia oil, jojoba oil, rice germ oil, glycerol trioctanate, glycerol triisopalmiatate, trimethylolpropane triisostearate, isopropyl myristate, glycerol tri-2-ethylhexanoate, pentaerythritol tetra-2-ethylhexanoate, lanolin, liquid lanolin, liquid paraffin, squalane, vaseline, and mixtures thereof. Commercially available oils include, for example, tridecyl isononanoate with tradename Crodamol TN available from Croda, Hexalan available from Nisshin Seiyu, and tocopherol acetates available from Eisai.

Non-volatile oils useful herein also include polyalkyl or polyaryl siloxanes with the following structure (I)

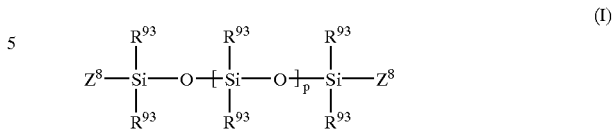

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the skin, is compatible with the other components of the composition, and is chemically stable under normal use and storage conditions. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Non-volatile oils also useful herein are the various grades of mineral oils. Mineral oils are liquid mixtures of hydrocarbons that are obtained from petroleum. Specific examples of suitable hydrocarbons include paraffin oil, mineral oil, dodecane, isododecane, hexadecane, isohexadecane, eicosene, isoeicosene, tridecane, tetradecane, polybutene, polyisobutene, and mixtures thereof.

Non-volatile oils particularly useful herein are those which have relatively low viscosity. Such low viscosity non-volatile oils are believed to enhance the fresh and light feel when the composition is applied to the skin.

Thickening Agents

The composition of the present invention may further contain a thickening agent for providing a viscous liquid or solid composition, such as solid waxes, gelling agents, inorganic thickeners, oil soluble polymers, fatty compounds, and mixtures thereof. As necessary, the thickening agent is comprised by weight of the entire composition at from about 0.5% to about 20%, preferably from about 1% to about 15%.

For providing solid compositions, a solid wax is preferably used. The amount of the solid wax is controlled to provide the desired hardness and strength to the product. The solid waxes useful herein are paraffin wax, microcrystalline wax, ozokerite was, ceresin wax, carnauba wax, candelilla wax, eicosanyl behenate, and mixtures thereof. A mixture of waxes is preferably used. Commercially available solid waxes useful herein include: Candelilla wax NC-1630 available from Noda wax, Ozokerite wax SP-1021 available from Strahl & Pitsh, and Eicosanyl behenate available from Cas Chemical.

Gelling agents may be included in the carrier as a thickening agent. Gelling agents include esters and amides of fatty acid gellants, hydroxy acids, hydroxy fatty acids, cholesterolic materials, lanolinolic materials, other amide gellants, and crystalline gellants. N-acyl amino acid amides useful herein are prepared from glutamic acid, lysine, glutamine, aspartic acid and mixtures thereof. Particularly preferred are n-acyl glutamic acid amides corresponding to the following formula:

$$R^2-NH-CO-(CH_2)_2-CH-(NH-CO-R^1)-CO-NH-R^2$$

wherein $R^1$ is an aliphatic hydrocarbon radical having from about 12 to about 22 carbon atoms, and $R^2$ is an aliphatic hydrocarbon radical having from about 4 to about 12 carbon atoms. Non-limiting examples of these include n-lauroyl-L-glutamic acid dibutyl amide, n-stearoyl-L-glutamic acid diheptyl amide, and mixtures thereof. Most preferred is n-lauroyl-L-glutamic acid dibutyl amide, also referred to as dibutyl lauroyl glutamide. This material is commercial available with tradename Gelling agent GP-1 available from Ajinomoto. Amidoamines of the following general formula are useful herein:

$$R^1CONH(CH_2)_mN(R^2)_2$$

wherein $R^1$ is a residue of $C_{11}$ to $C_{24}$ fatty acids, $R^2$ is a $C_1$ to $C_4$ alkyl, and m is an integer from 1 to 4. Preferred amidoamine useful in the present invention includes stearamidopropyidimethylamine, stearamidopropyldiethylamine, stearamidoethyldiethylamine, stearamidoethyldimethylamine, palmitamidopropyldimethylamine, palmitamidopropyidiethylamine, palmitamidoethyidiethylamine, palmitamidoethyldimethylamine, behenamidopropyidimethylamine, behenamidopropyldiethylamine, behenamidoethyldiethylamine, behenamidoethyidimethylamine, arachidamidopropyidimethylamine, arachidamidopropyldiethylamine, arachidamidoethyldiethylamine, arachidamidoethyldimethylamine, and mixtures thereof; more preferably stearamidopropyldimethylamine, stearamidoethyldiethylamine, and mixtures thereof. Other gelling agents suitable for use in the compositions include 12-hydroxystearic acid, esters of 12-hydroxystearic acid, amides of 12-hydroxystearic acid and combinations thereof. These preferred gellants include those which correspond to the following formula:

$$R^1-CO-(CH_2)_{10}-CH-(OH)-(CH_2)_5-CH_3$$

wherein $R^1$ is $R^2$ or $NR^2R^3$; and $R^2$ and $R^3$ are hydrogen, or an alkyl, aryl, or arylalkyl radical which is branched linear or cyclic and has from about 1 to about 22 carbon atoms; preferably, from about 1 to about 18 carbon atoms. $R^2$ and $R^3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, triester of glycerin and hydroxystearic acid known as trihydroxystearin, and mixtures thereof; even more preferably, 12-hydroxystearic acid, isopropyl amide of 12-hydroxystearic acid, and combinations thereof.

Commercially available hydroxystearin compounds useful herein include 12-hydroxystearic acid (cosmetic grade) available from Kawaken and CasChem, and trihydroxystearin with tradenames Thixcin R available from Rheox, Flowtone R available from ECC America, and Rheocin available from United Catalysts. Suitable amide gellants include disubstituted or branched monoamide gellants, monosubstituted or branched diamide gellants, triamide gellants, and combinations thereof, excluding the n-acyl amino acid derivatives selected from the group consisting of n-acyl amino acid amides, n-acyl amino acid esters prepared from glutamic acid, lysine, glutamine, aspartic acid, and combinations thereof, and which are specifically disclosed in U.S. Pat. No. 5,429,816.

Alkyl amides or di- and tri-basic carboxylic acids or anhydrides suitable for use in the composition include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene-1,2,3-triotylamide, N,N',N"-tri(acetodecylamide)amine, 2-dodecyl-N,N'-dihexylsuccinamide, and 2 dodecyl-N,N'-dibutylsuccinamide. Preferred are alkyl amides of di-carboxylic acids such as di-amides of alkyl succinic acids, alkenyl succinic acids, alkyl succinic anhydrides and alkenyl succinic anhydrides, more preferably 2-dodecyl-N,N'-dibutylsuccinamide.

Other gellants useful herein include anthryl derivatives such as 2,3-bis n-decyloxyanthracene, hybrids of steroids and anthryl derivatives such as cholesterol anthraquinone-2-carboxylate, alpha amino acid oligomers such as N-benzyl oxycarbonyl-l-valyl-L-valine-n-octadecyl amide, organometallics such as mononuclear copper beta-diketonates and binulclear Cu and Rh tetracarboxylates, dextrin derivatives such as dextrin palmitate and dextrin myristate, and decaglycerin pentastearic acid.

Inorganic thickeners useful as thickening agents herein include oil swelling clays, oil soluble clays, silica, and mixtures thereof. The oil swelling clay material useful herein are those which function as a thickener for the composition. Thus, the amount of oil swelling clay material included is adjusted depending on the desired viscosity and hardness of the composition. For providing lipstick compositions, the oil swelling clay material is comprised by weight of the entire composition at from about 0.1% to about 1%, preferably from about 0.2% to about 0.5%. Oil swelling clay materials useful herein include hectorite, bentonite, montmorillonite, and bentone clays which have been modified to be compatible with oil. Preferably, the modification is quaternization with an ammonium compound. Preferable oil swelling clay materials include quaternary ammonium modified hectorite. Commercially available oil swelling clay materials include benzyldimethyl stearyl ammonium hectorite with tradename Bentone 38 CG OR available from Rheox. Inc. The silica thickening agents commercially available are the Aerosil series (200, 300, 200CF, and 300CF) available from Degussa.

Oil soluble polymers are useful as thickeners. Oil soluble polymers useful herein include guar gum which is a resinous material derived from the ground endosperm of cyanopsis tetragonoloba and close relatives.

Fatty compounds are useful as thickening agents. The fatty compound useful herein have a melting point of 25° C. or higher, and is selected from the group consisting of fatty alcohols, fatty acids, fatty alcohol derivatives, fatty acid derivatives, and mixtures thereof. It is understood that the fatty compound thickeners herein may also provide emollient benefits.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof. Fatty acid soaps are also useful herein. Nonlimiting examples of fatty acid soaps include natural soaps with Li, Na, Ca. Ba, and Al metals, including aluminium oleate and aluminium laurate.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$–$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Commercially available materials useful herein include: myristyl myristate available from Croda with tradename Crodamol MM; cetyl alcohol, stearyl alcohol, and behenyl alcohol having tradenames KONOL series available from Shin Nihon Rika (Osaka, Japan), and NM series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy).

Fatty compounds useful herein include fatty acid sugar esters having $C_{1-30}$ monoester or polyester of sugars and one or more carboxylic acid moieties, preferably a sucrose polyester in which the degree of esterification is 7–8, and in which the fatty acid moieties are $C_{18}$ mono- and/or di-unsaturated and behenic, in a molar ratio of unsaturates:behenic of 1:7 to 3:5, more preferably the octaester of sucrose in which there are about 7 behenic fatty acid moieties and about 1 oleic acid moiety in the molecule, e.g., sucrose ester of cottonseed oil fatty acids. The thickening capability of these compounds are futher enhanced by adding about 1–3% of lower alcohols such as ethanol in the composition. Preferred compounds in this group include sucrose esterified with fatty acids derived from hardened, high-erucic acid rapeseed oil coded as SEFA behenate available from the Procter & Gamble Company. Fatty compounds useful herein include aluminium salt of phosphatidic acid, steroid derivatives, cholesterol esters, and Na, Li, K, and NH4 salts of 12-hydroxyoctadecanoic acid.

Skin Treatment Agent

The composition of the present invention may further comprise a skin treatment agent by weight of the entire composition at from about 0.5% to about 5%, preferably from about 1% to about 5%.

Skin treatment agents useful herein are niacinamide, panthenol, and mixtures thereof. Niacinamide is particularly preferred in that, when used in a pharmaceutically effective amount, is capable of reducing or alleviating the intensity of chronical spots. Niacinamide is suitably incorporated in the composition by first dissolving in water. Niacinamide and panthenol are commercially available, for example, by Roche.

Humectant

The composition of the present invention may further comprise a humectant by weight of the entire composition at from about 0.1% to about 20%, preferably from about 1% to about 10%.

The humectants herein are selected from the group consisting of polyhydric alcohols, water soluble alkoxylated nonionic polymers, and mixtures thereof.

Polyhydric alcohols useful herein include glycerin, propylene glycol, 1,3-butylene glycol, dipropylene glycol, diglycerin, sodium hyaluronate, and mixtures thereof.

Commercially available humectants herein include: glycerin available from Asahi Denka; propylene glycol with tradename LEXOL PG-865/855 available from Inolex, 1,2-PROPYLENE GLYCOL USP available from BASF; 1,3-butylene glycol available from Daisel Kagaku Kogyo; dipropylene glycol with the same tradename available from BASF; diglycerin with tradename DIGLYCEROL available from Solvay GmbH; sodium hyaluronate with tradenames ACTIMOIST available from Active Organics, AVIAN SODIUM HYALURONATE series available from Intergen, HYALURONIC ACID Na available from lchimaru Pharcos.

Lipophilic Surfactant

The composition of the present invention may further comprise a lipophilic surfactant by weight of the entire composition at from about 1% to about 5%, preferably 1% to about 3%. The lipophilic surfactant herein has an HLB value of less than about 8.

The HLB value is a theoretical index value which describes the hydrophilicity-hydrophobicity balance of a specific compound. Generally, it is recognized that the HLB index ranges from 0 (very hydrophobic) to 40 (very hydrophilic). The HLB value of the lipophilic surfactants may be found in tables and charts known in the art, or may be calculated with the following general equation: HLB=7+ (hydrophobic group values)+(hydrophilic group values). The HLB and methods for calculating the HLB of a compound are explained in detail in "Surfactant Science Series, Vol. 1: Nonionic Surfactants", pp 606–13, M. J. Schick (Marcel Dekker Inc., New York, 1966).

The lipophilic surfactant can be an ester-type surfactant. Ester-type surfactants useful herein include: sorbitan monoisostearate, sorbitan diisostearate, sorbitan sesquiisostearate, sorbitan monooleate, sorbitan dioleate, sorbitan sesquioleate, glyceryl monoisostearate, glyceryl diiosostearate, glyceryl sesquiisostearate, glyceryl monooleate, glyceryl dioleate, glyceryl sesquioleate, diglyceryl diisostearate, diglyceryl dioleate, diglycerin monoisostearyl ether, diglycerin diisostearyl ether, and mixtures thereof.

Commercially available ester-type surfactants are, for example, sorbitan isostearate having a tradename Crill 6 available from Croda, and sorbitan sesquioleate with tradename Arlacel 83 available from Kao Atras.

The lipophilic surfactant can be a silicone-type surfactant. Silicone-type surfactants useful herein are (i), (ii), as shown below, and mixtures thereof.

(i) dimethicone copolyols having the structure:

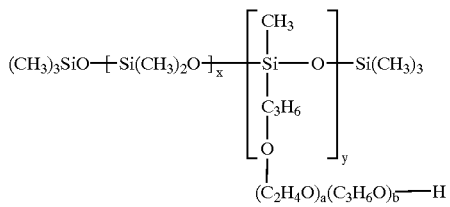

wherein x is an integer from 5 to 100, y is an integer from 1 to 50, a is zero or greater, b is zero or greater, the average sum of a+b being 1–100.

(ii) dimethicone copolyols having the structure:

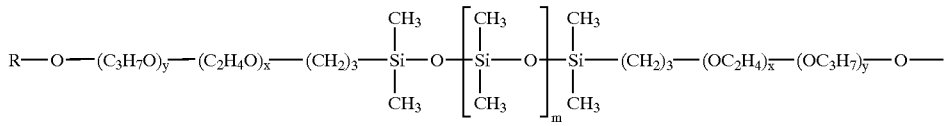

wherein R is selected from the group consisting of hydrogen, methyl, and combinations thereof, m is an integer from 5 to 100, x is independently zero or greater, y is independently zero or greater, the sum of x+y being 1–100.

Commercially available silicone-type surfactants are, for example, DC5225C, BY22-012, BY22-008, SH3746M, SH3771M, SH3772M, SH3773M, SH3775M, SH3748, SH3749, and DC5200, all available from Dow Corning.

Alkyl dimethicone copolyols are also useful as liphophilic surfactants. Suitable alkyl dimethicone copolyols comprise a methylpolysiloxane moiety, an alkyl methylpolysiloxane moiety, and a poly(oxyalkylene)methylpolysiloxane moiety; having an HLB from about 4 to about 6, and a molecular weight of from about 10,000 to about 20,000, wherein the alkyl group is made of from about 10 to about 22 carbons. The HLB value is a theoretical index value which describes the hydrophilicity-hydrophobicity balance of a specific compound. Generally, it is recognized that the HLB index ranges from 0 (very hydrophobic) to 40 (very hydrophilic). The HLB value of the lipophilic surfactants may be found in tables and charts known in the art, or may be calculated with the following general equation: HLB=7+(hydrophobic group values)+(hydrophilic group values). The HLB and methods for calculating the HLB of a compound are explained in detail in "Surfactant Science Series, Vol. 1: Nonionic Surfactants", pp 606–13, M. J. Schick (Marcel Dekker Inc., New York, 1966).

Suitable alkyl dimethicone copolyols herein are those which have the following formulation (I):

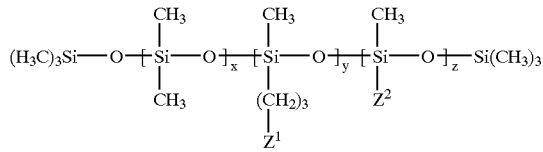

wherein $Z^1$ is $O(C_2H_4O)_p(C_3H_6O)_qH$, p is from 0 to about 50, q is from 0 to 30, wherein p and q are not 0 at the same time; x is from 1 to about 200, y is from 1 to about 40, and z is from 1 to about 100, and $Z^2$ is an alkyl group having from about 10 to about 22 carbons, preferably from about 16 to about 18 carbons.

Highly preferred alkyl dimethicone copolyols include cetyl dimethicone copolyol and stearyl dimethicone copolyol. A highly preferred commercially available alkyl dimethicone copolyol includes cetyl dimethicone copolyol, also called Methylpolysiloxane Cetylmethylpolysiloxane Poly(oxyethylene oxypropylene) Methylpolysiloxane Copolymer, having an HLB of about 5 and a molecular weight of about 13,000 having a tradename ABIL EM90 available from Goldschmidt Personal Care.

In a preferred embodiment, the lipophilic surfactant is a mixture of at least one ester-type surfactant and at least one silicone-type surfactant to provide a stable emulsion for the other essential components of the present invention.

Pigments

The composition of the present invention may further comprise a pigment by weight of the entire composition at less than about 10%, preferably less than about 5%. Pigments useful herein include color pigments and white pigments.

The pigments are selected depending on the desired characteristic of the product, for example, shade, coverage, and various skin feel. Such pigments may be preferred for use when the composition is a foundation base for providing a certain tone to the skin.

In a preferred embodiment, when color pigments are used, they are used at a level by weight of the entire composition of less than about 3%. For example, for providing a foundation base product, the amount of color pigments should be controlled to avoid unnecessary color interference with the foundation.

The color pigments useful herein are iron oxide, iron titanate, ultramarine blue, Prussian blue, chromium oxide, chromium hydroxide, cobalt oxide, cobalt titanate, titanium oxide coated mica; organic powders such as fish scale guanine, laked tar color dyes, and laked natural color dyes. Such color pigments may be treated with a hydrophobic treatment agent, including: silicone such as Methicone, Dimethicone and perfluoroalkylsilane; fatty material such as stearic acid; metal soap such as aluminium dimyristate; aluminium hydrogenated tallow glutamate, hydrogenated lecithin, lauroyl lysine, aluminium salt of perfluoroalkyl phosphate, and mixtures thereof.

White pigments that are not of UV-protection grade, have thickening properties, or have less oil absorbing ability than required for the non-thickening oil absorbing powders, may also be useful. Such pigments include titanium dioxide, and zinc oxide, talc, mica, sericite, silica, magnesium silicate, synthetic fluorphlogopite, calcium silicate, aluminum silicate, bentonite and montomorilonite; pearl pigments such as alumina, barium sulfate, calcium secondary phosphate, calcium carbonate, titanium oxide, finely divided titanium oxide, zirconium oxide, zinc oxide, hydroxy apatite, and those treated with the hydrophobic treatment agents mentioned above.

Additional Components

Other components which can be formulated into the compositions of the present invention are; preservatives such as benzyl alcohol, methyl paraben, propyl paraben, imidazolidinyl area, and EDTA and its salts, perfumes, infrared screening and absorbing agents, film forming polymers such as polyvinyl pyrrolidone, guai azulene, saccharomycopsis ferment filtrate, coix lacryma-jobi (job's tears) seed extract and others.

Process

The composition of the present invention may be made by a method well known in the art. In a suitable process, the composition is made by the steps of:

1) heating and dissolving the volatile silicone oil, non-volatile oil, and if present, thickening agents lipophilic surfactant, and any other oil phase material having a high melting point to about 80–85° C. in a sealed tank, to make a lipophilic mixture;
2) adding the non-thickening oil absorbing powders into such liphophilic mixture and dispersing with a homogenizer at about 75–80° C.;
3) separate from 1) and 2), heating and dissolving in water, skin treatment agents, humectants, when present, and any other hydrophilic material to about 75–80° C.;
4) adding the product of step 2) to the product of step 3) to effect an emulsification; and
5) cooling the obtained emulsion to room temperature.

The obtained composition is filled in an air-tight container.

Method of Use

The composition of the present invention is in the form of a water-in-oil emulsion that can be made into fluids of various viscosity, and or solids. The sunscreen composition of the present invention provides effective UV protection benefit, while leaving a fresh, cool, non-greasy feeling to the skin, even for consumers having oily skin. Further, in view of the presence of the non-thickening oil absorbing powders, the sunscreen composition of the present invention provides a matte finish, which is an appearance appreciated by consumers having oily skin. In view of these unique benefits, the sunscreen composition of the present invention is suitable for daily use sunscreen products, particularly for consumers having oily skin.

The sunscreen composition of the present invention is also suitable for use as a foundation base product, in that the composition can be spread evenly and provide a matte finish, improved shine control, and has controlled affinity and solubility with foundation products.

By adding a selected thickening agent, preferably a solid wax, the composition of the present invention may be made into a solid. By providing such a solid composition in a compact, the composition may be applied to the skin using a buff. By providing such a solid composition as a stick, the composition may be applied to the skin directly, without using the hands or fingers. Thus, a sunscreen composition which is easy to apply and not messy upon use can be obtained. Further, such packaging forms are suitable for the consumer to carry.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Examples 1–6

| NO. | Component | Ex. 1 | Ex. 2 | Ex. 3 | Ex. 4 | Ex. 5 | Ex. 6 |
|---|---|---|---|---|---|---|---|
| 1 | Cyclomethicone | 38.0 | 36.0 | 33.0 | 33.0 | 33.0 | 34.0 |
| 2 | Isotridecyl isononanoate *1 | 2.0 | 2.0 | 2.0 | 4.0 | 2.0 | 2.0 |
| 3 | Octyl Methoxycinnamate *2 | 4.0 | 4.0 | 8.0 | 3.0 | 2.0 | 4.0 |
| 4 | 4-tert-Butyl-4'-methoxy dibenzoylmethane *3 | 0.5 | | | 0.5 | | |
| 5 | Tocopherol acetate | 0.5 | 0.5 | 0.5 | 0.5 | 0.5 | 0.5 |
| 6 | Candelilla wax | 1.0 | 1.0 | | 0.4 | | 3.2 |
| 7 | Ozokerite wax | 3.0 | 2.7 | | 2.0 | 2.0 | |
| 8 | Cetyl Alcohol | | | 3.0 | 3.0 | 3.0 | |
| 9 | Sorbitan isostearate *4 | | 2.0 | | | | 2.0 |
| 10 | Cetyl Dimethicone Copolyol *5 | | | 2.0 | 2.0 | 2.0 | |
| 11 | Dimethicone copolyol *6 | 1.2 | 1.2 | 1.2 | | 1.2 | 1.2 |
| 12 | Crosslinked silicone powder *7 | | | | 2.0 | | |
| 13 | Trimethyl siloxy silicate *8 | | | | | 1.0 | |
| 14 | Dimethicone Treated Silica *9 | 20.0 | 13.0 | 13.0 | | | 14.4 |
| 15 | Boron Nitride *10 | | | | 15.0 | 13.0 | |
| 16 | Methicone and Aluminium Hydroxide Treated Micro Titanium Dioxide *11 | 2.0 | 2.0 | | 2.0 | 5.0 | 2.3 |
| 17 | Dimethicone and Myristic Acid Treated Micro Zinc Oxide *12 | 3.0 | 3.0 | 3.0 | | 3.0 | |
| 18 | Deionized water | | | q.s. to 100% | | | |
| 19 | Niacinamide *13 | 2.0 | 2.0 | 2.0 | 2.0 | 2.0 | 2.0 |
| 20 | Panthenol *14 | 0.25 | 0.25 | 0.25 | 0.25 | 0.25 | 0.25 |
| 21 | Preservative | 0.5 | 0.5 | 0.5 | 0.5 | 0.5 | 0.5 |
| 22 | 1,3 Butylene glycol | 5.0 | 5.0 | | 5.0 | 5.0 | 5.0 |

-continued

| NO. | Component | Ex. 1 | Ex. 2 | Ex. 3 | Ex. 4 | Ex. 5 | Ex. 6 |
|---|---|---|---|---|---|---|---|
| 23 | Guai-azulene *15 | | 0.1 | 0.1 | 0.1 | | |
| 24 | Saccharomycopsis Ferment Filtrate *16 | | | 15.0 | | 10.0 | |
| 25 | Glycerine | | | 5.0 | | | |
| 26 | Polyvinylpyrrolidone *17 | | | | 0.5 | | |
| 27 | Sodium Chloride | | | 0.5 | 0.5 | | 0.5 |
| 28 | Microcrystalline Wax | | | | | | 1.6 |
| 29 | Coix Lacryma-jobi (Job's Tears) Seed Extract *18 | | | | | | 1.0 |
| 30 | Methicone Treated Micro Zinc Oxide *19 | | | | | | 1.3 |

Definitions of Components
*1 Isotridecyl isononanoate: Crodamol TN available from Croda
*2 Octyl Methoxycinnamate: Parsol MCX available from Givaudan
*3 4-tert-Butyl-4'-methoxy dibenzoylmethane: Parsol 1789 available from Givaudan
*4 Sorbitan isostearate: Crill 6 available from Croda
*5 Cetyl Dimethicone Copolyol: Abil EM90 available from Goldshmidt
*6 Dimethicone copolyol: DC5225C available from Dow Corning
*7 Crosslinked silicone powder: Torayfil E-506C available from Dow Corning
*8 Trimethylsiloxy silicate: BY11-018 available from Dow Corning
*9 Dimethicone Treated Silica: SASB-300 (7%) available from Miyoshi Kasei. The oil absorbency is 130.4 ml/100 g.
*10 Boron Nitride: available from Toray. The oil absorbency is 95.2 ml/100 g.
*11 Methicone and Aluminium Hydroxide Treated Micro Titanium Dioxide: SI-TTO-S-3-Z LHC available from Miyoshi Kasei.
*12 Dimethicone and Myristic Acid Treated Micro Zinc Oxide: SAMT-UFZO-450 available from Miyoshi Kasei.
*13 Niacinamide: Niacinamide available from Roche
*14 Panthenol: DL-Panthenol available from Roche
*15 Guai-azulene: available from Konan Kako
*16 Saccharomycopsis Ferment Filtrate: SK-II Pitera available from Kashiwayama
*17 Polyvinylpyrrolidone: PVP K-30 available from GAF Chemicals
*18 Coix Lacryma-jobi (Job's Tears) Seed Extract: Coix Seed Extract available from Koei Kogyo
*19 Dimethicone Treated Micro Zinc Oxide: Z-Cote HP-1 available from BASF Method of Preparation The compositions of Examples 1–2 and 6 are prepared as follows: component numbers 1 through 13 and 28, as present, are heated to dissolve at 82° C. in a sealed tank, followed by adding component number 14 through 17 and 30, and the mixture is dispersed at 80° C. using a homogenizer to make a lipophilic mixture. Separately, a mixture of component numbers 18 through 24, 27 and 29, as present, are heated to dissolve at 80° C. and added to the lipophilic mixture to effect an emulsification. The obtained emulsion is adjusted to a temperature of 70° C. Finally, the emulsion is filled in an air-tight container and allowed to cool to room temperature using a cooling unit. The compositions of Examples 1, 2 and 6 provide a solid composition.

The compositions of Examples 3–5 are prepared as follows: component numbers 1 through 13, as present, are heated to dissolve at 82° C. in a sealed tank, followed by adding component number 14 through 17, and the mixture is dispersed at 80° C. using a homogenizer to make a lipophilic mixture. Separately, a mixture of component numbers 18 through 24, as present, are heated to dissolve at 80° C. and added to the lipophilic mixture to effect an emulsification. The obtained emulsion is mixed and is cooled to 30° C. If necessary, the emulsion mixed using homogenizer at 30–40° C. Finally, the emulsion is filled in an air-tight container. The compositions of Examples 3–5 provide a cream.

These embodiments represented by the previous examples have many advantages. For example, they can provide effective UV protection benefit, while leaving a fresh, cool, non-greasy feeling to the skin, even for consumers having oily skin. All embodiments can be used as foundation base products.

What is claimed is:

1. A water-in-oil emulsified sunscreen composition comprising by weight:
    (a) an effective amount of a UV protection agent;
    (b) from about 0.1% to about 70% of a non-thickening oil absorbing powder having a mineral oil absorbing ability of at least about 40 ml/100 g;
    (c) at least about 10% of the entire composition of water; and
    (d) an oil phase comprising:
        (i) at least about 50% by weight of the oil phase of a volatile silicone oil; and
        (ii) from about 0.1% to less than the oil absorbing ability of the non-thickening oil absorbing powder of a non-volatile oil; wherein when the UV protection agent is a non-volatile liquid of hydrophobic nature, it is considered the non-volatile oil.

2. The water-in-oil emulsified sunscreen composition according to claim 1 further comprising from about 0.5% to about 20% by weight of the entire composition of a thickening agent.

3. The water-in-oil emulsified sunscreen composition according to claim 2 wherein the thickening agent is a solid wax.

4. The water-in-oil emulsified sunscreen composition according to claim 1 further comprising from about 0.5% to about 5% of a skin treatment agent.

5. The water-in-oil emulsified sunscreen composition according to claim 1 further comprising from about 0.1% to about 20% of a humectant.

6. The water-in-oil emulsified sunscreen composition according to claim 1 further comprising from about 1% to about 5% of a lipophilic surfactant.

7. The water-in-oil emulsified sunscreen composition according to claim 1 further comprising a pigment, wherein the level of color pigments is at a level by weight of the entire composition of less than about 3%.

8. The water-in-oil emulsified sunscreen composition of claim 1 comprising by weight:
   (a) from about 1% to about 20% of a UV protection agent;
   (b) from about 5% to about 30% of a non-thickening oil absorbing powder having a mineral oil absorbing ability of at least 40 ml/100 g;
   (c) from about 10% to about 40% of the entire composition of water;
   (d) an oil phase comprising:
      (i) at least about 70% by weight of the oil phase of a volatile silicone oil;
      (ii) from about 0.1% to about 30% of non-volatile oil; wherein when the UV protection agent is non-volatile and hydrophobic, it is considered the non-volatile oil; and
   (e) from about 0.5% to about 20% of a solid wax;
   (f) from about 0.5% to about 5% of the skin treatment agent; and
   (g) from about 1% to about 10% of a humectant.

9. A method of improving the performance of a foundation comprising the step of applying to the skin the composition of any of claims 1 through 8 to the skin, prior to applying the foundation.

* * * * *

UNITED STATES PATENT AND TRADEMARK OFFICE
CERTIFICATE OF CORRECTION

PATENT NO. : 6,936,241 B2
DATED : August 30, 2005
INVENTOR(S) : Yamada et al.

It is certified that error appears in the above-identified patent and that said Letters Patent is hereby corrected as shown below:

Column 3,
Line 15, "butylmethoxyd ibenzoyl-methane" should read -- butylmethoxydibenzoyl-methane --.

Column 9,
Line 29, "stearamidopropyidimethylamine" should read
-- stearamidopropyldimethylamine --.
Line 32, "palmitamidopropyidiethylamine" should read
-- palmitamidopropyldiethylamine --.
Lines 32-33, "palmitamidoethyidiethylamine" should read
-- palmitamidoethyldiethylamine --.
Lines 33-34, "behenamidopropyidimethylamine" should read
-- behenamidopropyldimethylamine --.
Lines 35-36, "behenamidoethyidimethylamine" should read
-- behenamidoethyldimethylamine --.
Line 36, "arachidamidopropyidimethylamine" should read
-- arachidamidopropyldimethylamine --.

Column 14,
Line 15, "to 30" should read -- to about 30 --.

Signed and Sealed this

First Day of November, 2005

JON W. DUDAS
*Director of the United States Patent and Trademark Office*